United States Patent [19]

Tanaka et al.

[11] Patent Number: 5,098,722

[45] Date of Patent: * Mar. 24, 1992

[54] METHOD OF MANUFACTURING IRON-FORTIFIED BEVERAGE

[75] Inventors: Maki shi Tanaka; Teiichi Tojima; Shun-ichi Dousako; Kiyoshi Tatsumi, all of Saitama, Japan

[73] Assignee: Snow Brand Milk Products Co., Ltd., Hokkaido, Japan

[*] Notice: The portion of the term of this patent subsequent to Apr. 16, 2008 has been disclaimed.

[21] Appl. No.: 690,542

[22] Filed: Apr. 23, 1991

[30] Foreign Application Priority Data

Apr. 26, 1990 [JP] Japan .................................. 2-110952

[51] Int. Cl.⁵ .......................................... A23L 1/304
[52] U.S. Cl. ...................................... 426/74; 426/590
[58] Field of Search ................................. 426/74, 590

[56] References Cited

U.S. PATENT DOCUMENTS

| | | | |
|---|---|---|---|
| 4,402,938 | 9/1983 | Collins | 426/583 |
| 4,667,018 | 5/1987 | Prieells | 426/656 |
| 4,726,948 | 2/1988 | Prieels | 426/658 |
| 4,762,822 | 8/1988 | Ettinger | 426/532 |
| 4,791,193 | 12/1988 | Okonogi | 426/657 |
| 4,834,994 | 5/1989 | Kuwata | 426/271 |
| 4,919,961 | 4/1990 | Lundblad | 426/648 |
| 4,944,944 | 7/1990 | Tang | 426/2 |
| 4,946,944 | 8/1990 | Frankinet | 426/657 |
| 5,008,120 | 4/1991 | Tanaka | 426/74 |

FOREIGN PATENT DOCUMENTS 364912 5/1979 European Pat. Off.

Primary Examiner—Carolyn Paden
Attorney, Agent, or Firm—Burgess, Ryan and Wayne

[57] ABSTRACT

The method of manufacturing either aqueous soltuion of lactoferin, iron preparation and sodium bicarbonate. or aqueous solution of iron lactoferrin; and adjusting its electric conducitivity (ΩmS/cm) and its hydrogen ion concentration (pH) so that it meets the conditions provided by the formulae that follow; pasteurizing by heat; and manufacturing iron-fortified beverage using above materials; and having high bioavailability of iron and maintaining physiological functions of lactofe-rrin.

$$\log \Omega \leq \frac{2.96}{pH} + 0.64 \; pH < 5$$

$$\log \Omega \leq \frac{29.37}{pH} - 4.62 \; 5 \leq pH \leq 7.9$$

$$\log \Omega \leq -0.917 \; pH > 7.9$$

5 Claims, 4 Drawing Sheets

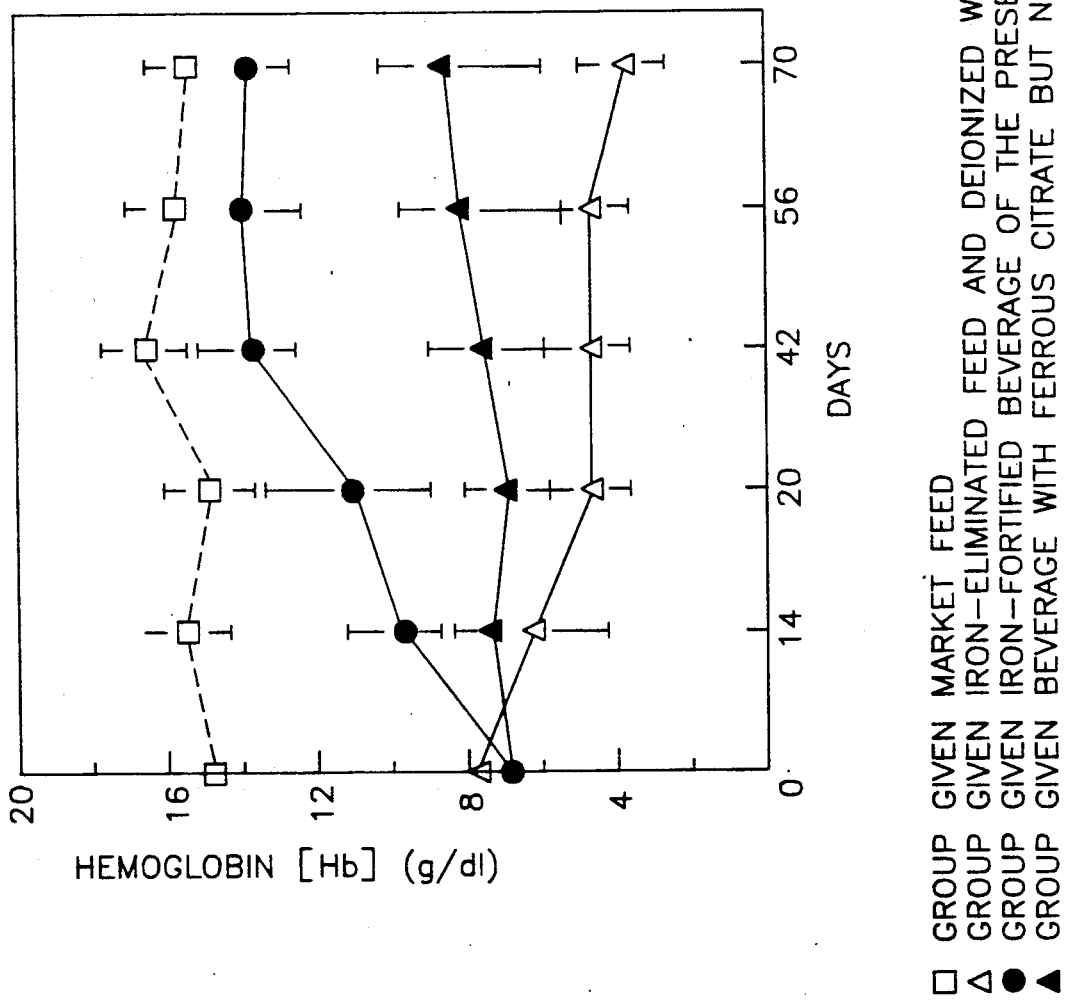

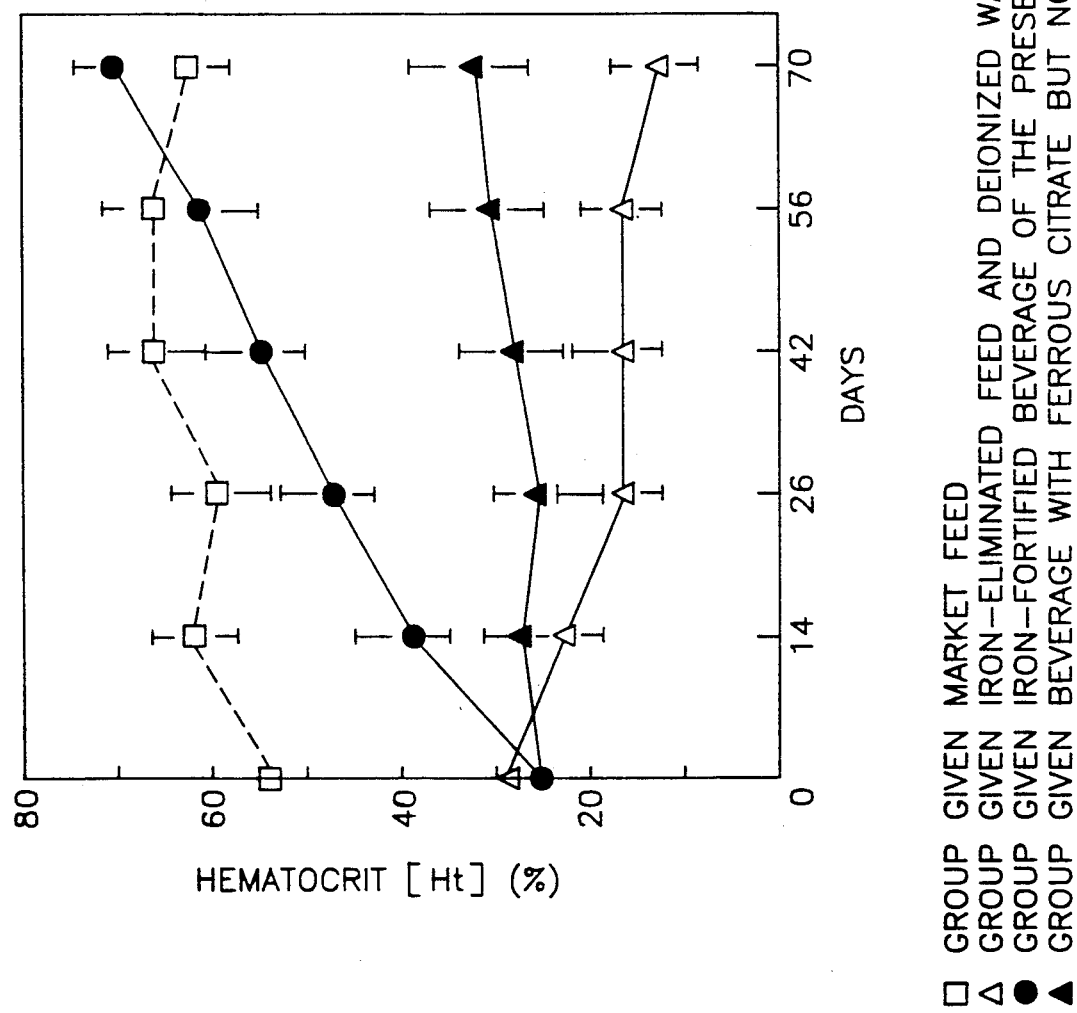

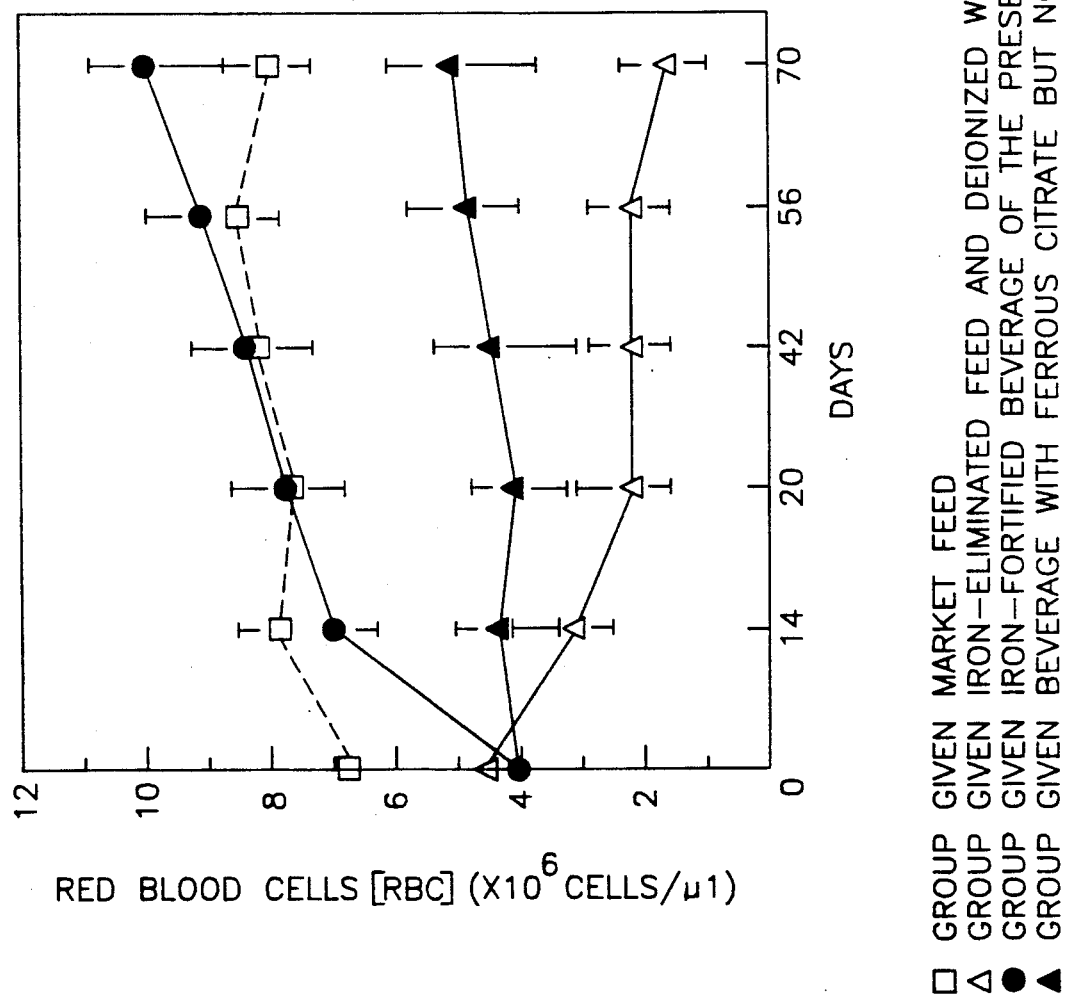

METHOD OF MANUFACTURING IRON-FORTIFIED BEVERAGE

BACKGROUND OF THE INVENTION

The present invention relates to a method of manufacturing iron-fortified beverage; particulaly a method of manufacturing iron-fortified bevarage containing lactoferrin capable of binding iron.

DESCRIPTION OF THE PRIOR ART

The iron recommended daily allowance of women over thirteen years old is 12 mg. However, according to Japan national nutrition survey in 1987, average iron intake is 10.6 mg/day on the adult women and 8.0 mg/day on the high school girl, therefore, it is thought that the iron intake has a tendency to be deficient on the women, especially on the young women. Various iron-supplement foods are now on the market, but they can not be employing generally owing to the form of beverage and the flavor.

Well known iron-fortification materials are inorganic iron such as sodium ferrous citrate, ferrous pyrophosphate, ferrous sulfate and ferrous ammonium citrate and organic iron such as heme-iron. The inorganic irons are not desirable physiologically as iron-fortified ingredients, according to the reason of about only 5% of bioavailability at the digestive tract, the formation of insolubles associated with fitic acid or tannic acid in the digestive tract, the tendency of inhibitory absorption at the digestive tract due to incorporation of iron into dietary fibers and the care of side effect by the large intakes all at once.

The inorganic iron is employed in various products owing to a good flavor and color in comparison with heme-iron.

On the other hand, although the heme-iron is desirable on the physiological effect as the ingredient according to 25~35% of bioavailability of iron and affecting hardly by other ingredients, a particular color and taste restrict the employment of heme-iron for foods.

For example, since heme-iron shows a dark brown, the particular color must be masked by mixing with food ingredients of black color lines such as iron-fortified food with coffee-taste (Japanese laid Open Paten Application 64-85056) or with raw sugar taste (Japanese laid Open Patent Application 64-85057). Moreover, the employment for food was restricted further according to remaining flavor derived from blood of slaughtered animal of source of heme-iron.

Recently developed is a hematopoietic preparation whose active ingredient is lactoferrin capable of binding iron, prepared by chelating ferric ion to lactoferrin separated from milk, and utilization of this hematopoietic preparation as ingredient for various food products and beverages has been proposed (Japanese laid Open Patent Application 63-22525).

However, when hematopoietics described above are used by adding to beverages and dissolving, one problem here is that beverages are required to be pasteurized by heat, which destroys the three dimensional structure of lactoferrin and causes precipitation, depriving lactoferrin of its inherent physiological functions and, eventually, of its capability to chelate iron.

Japanese Food Sanitation Law stipulates in its standards for processing soft drinks that they must be pasteurized; (1) by heat at 65° C. for 10 minutes, or by a method with equivalent effect, if the drink's pH is lower than 4.0, (2) by heat at 85° C. for 30 minutes, or by a method with equivalent effect, if the drink's pH is 4.0 to 4.6, (3) by heat at 120° C. for 4 minutes, or by a method with equivalent effect, if the drink's pH is more than 4.6, aqueous activity is more than 0.96, and storage at room temperature, (4) by heat at 85° C. for 30 minutes, or by a method with equivalent effect, if the drink's pH is more than 4.6, aqueous activity is more than 0.96, and storage at lower than 10° C.

Davidson and Lonnerdal (Am. J. Physiol. 257: G930–G934, 1989) has reported that the lactoferrin heated in boiling water at pH4.0 for 2 minutes has the same capacity on the iron binding with fresh lactoferrin. However, since actual foods have a high salt concentration, the lactoferrin can not be escaped to inactivation even if the pH was adjusted to acidic.

SUMMARY OF THE INVENTION

An object of the present invention relates to the method of manufacturing beverages that contain iron bound lactoferrin, which fortifys iron and which has high bioavailability of iron from the intestinal tract.

Another object of the present invention relates to the method of manufacturing beverages that contain iron-bound lactoferrin, which fortifys iron and which maintains physiological function of lactoferrin.

Yet another object of the present invention relates to the method of manufacturing beverages that contain iron-bound lactoferrin, which fortifys iron and which has good flavor.

These objects of the present invention are achieved by: preparing either aqueous solution of lactoferrin, iron preparation and sodium bicarbonate, or aqueous solution of iron lactoferrin; and adjusting its electric conductivity ($\Omega$ mS/cm) and its hydrogen ion concentration (pH) so that it meets the conditions provided by the formulae that follow; pasteurizing by heat; and then preparing iron-fortified beverage using above materials.

$$\log \Omega \leq \frac{2.96}{pH} + 0.64 \ pH < 5$$

$$\log \Omega \leq \frac{29.37}{pH} - 4.62 \quad 5 \leq pH \leq 7.9$$

$$\log \Omega \leq -0.917 \ pH > 7.9$$

BRIEF DESCRIPTION OF THE DRAWINGS

FIG. 2 shows changes of blood hemoglobin [Hb] level with the passage of days when the beverage of the present invention is given, together with the results of control.

FIG. 3 likewise shows the changes of hematocrit [Ht] level with the passage of days.

FIG. 4 likewise shows the change of the number of red blood cells [RBC] with the passage of days.

DETAILED DESCRIPTION OF PREFERRED EMBODIMENTS

Figure 1:
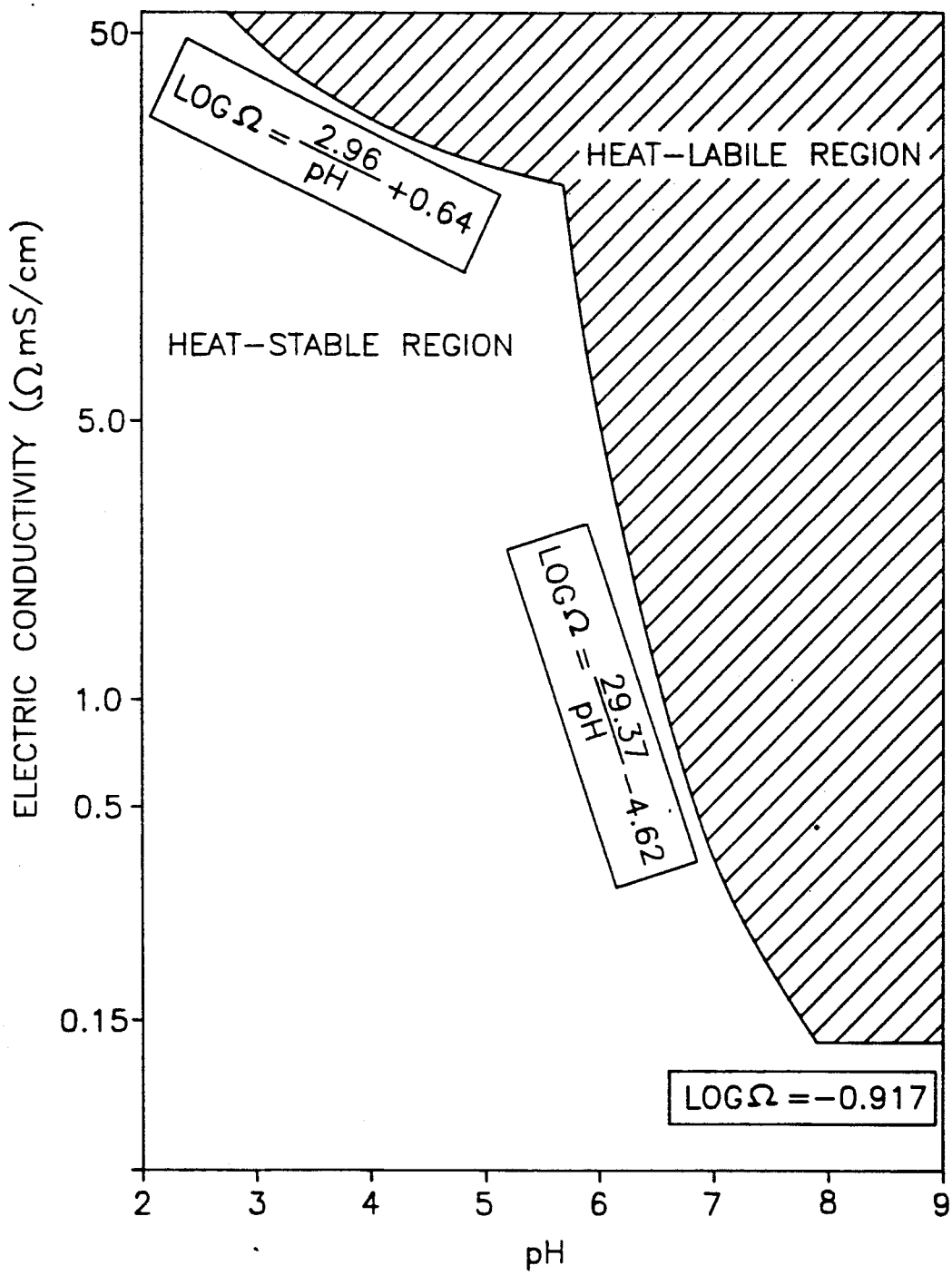
FIG. 1 indicates the relationship between the heat stability of lactoferrin, pH and electric conductivity.

Lactoferrin, used along with iron preparation in the present invention, is a glycoprotein capable of binding iron, which exists in exocrine such as milk and is a nutritionally and pharmacologically important milk protein.

Several methods to separate and purify lactoferrin have been known, including the method of using ion exchange resin (Gordon et al., Biochim. Biophys. Acta, 60: 410-411, 1962), the method adopting heparin-affinity chromatography (Blockerg et al., FEBS Lett., 109: 180, 1980), the method that uses affinity column immobilized with anti-lactoferrin monoclonal antibody (Laid Open Patent Application 61-145200), and the one using sulfuric esterified carrier (Laid Open Patent Application 63-255300). As long as lactoferrin is not denatured and is capable of binding iron, it obtained by any method may be used in the present invention.

In the present invention, either a mixed solution of lactoferrin, iron preparation and sodium bicarbonate or aqueous solution of iron lactoferrin is prepared, added other beverage ingredients and adjusted to meet the conditions of the following formulae, after which it is pasteurized by heat. Iron-fortified beverage was manufactured by the utilizations of these preparations as the raw materials.

$$\log \Omega \leq \frac{2.96}{pH} + 0.64 \ pH < 5$$

$$\log \Omega \leq \frac{29.37}{pH} - 4.62 \ \ 5 \leq pH \leq 7.9$$

$$\Omega \leq -0.917 \ pH > 7.9$$

If the solution to which all ingredient is dissolved does not satisfy the formulae indicated above, then the aqueous solution of lactoferrin is adjusted to meet the electric conductivity and the pH condition and pasteurized by heat. The remained ingredient was separately pasteurized by heat. The resultant both solutions were mixed in a sterilized tank and filled in containers to provide iron-fortified beverage.

Thus adjusting the electric conductivity according to each pH of the solution cantaining lactoferrin and then pasteurized by heat prevents denaturation of lactoferrin and maintains the functions.

The relationship between lactoferrin's iron-binding capacity, lactoferrin aqueous solution's electric conductivity and pH is shown in FIG. 1. Namely, the aqueous solution either containing lactoferrin, iron preparation and sodium bicarbonate or containing iron-lactoferrin is prepared. The said solution was adjusted with acetate buffer, phosphate buffer or glycine buffer to pH 2~9, and to electric conductivity of 0~50 Ω mS/cm, and heated at 60°~120° C. and tested the heat stability of lactoferrin or iron-lactoferrin. The lactoferrin or iron-lactoferrin was used as a concentration of 1%. The heat stability of stable or not was tested by deciding criterion of measurement on iron binding capability.

The result obtained under the heating temperature higher than 60° C., in spite of the concentration of lactoferrin or iron-lactoferrin was shown in FIG. 1. Namely, when the solution is pH<5, in the range of $$\log \Omega \leq \frac{2.96}{pH} + 0.64$$

when the solution is $5 \leq pH \leq 7.9$ in the range of $$\log \Omega \leq \frac{29.37}{pH} - 4.62$$

when the solution is pH>7.9 in the range of $$\log \Omega \leq -0.917$$

it was found that the lactoferrin in the solution is stable in the above range.

If the heating temperature is lower than 60° C., lactoferrin does not denature in the range of pH and electric conductivity of usual beverage and there is no need to adjust the electric conductivity, if the said temperature is 60° C. or higher and the electric conductivity does not satisfy the requirements indicatedon the said formulae, lactoferrin will lose some of its iron-binding capacity or may precipitate. Therefore, to pasteurize lactoferrin aqueous solution by heat, it is necessary to adjust to the electric conductivity which satisfy the requirements indicated on the said formulae.

In the present invention, desirable content of lactoferrin in beverage is 0.1~6% (or 0.1~6 g/100 ml). This lactoferrin content in the beverage is based on the supply of iron that coexists. As 1 g of lactoferrin supplies 1.5 mg of iron because of its iron-binding capacity, a lactoferrin content of less than 0.1% in the beverage means an iron supply of 0.15 mg/100 ml, which makes the beverage impractical as iron supplier since it is necessary to drink 700 ml or more /day to supply iron comparable to 1.0 mg of iron that is generally known to be excreted daily.

On the other hand, if lactoferrin content is more than 6% in the beverage, problems of processing arises because of increased viscosity and longer time needed to dissolve the greater amount of lactoferrin.

The lactoferrin content of 6% means an iron content of 9 mg/100 g beverage, which offers sufficient iron supply considering the high absorption ratio of iron lactoferrin. The lactoferrin concentration of less than 6% is desirable.

Then, it is desirable that the iron preparation or iron lactoferrin used in the present invention account for 0.15-12.0 mg as iron /100 ml of beverage. If the content of iron is below 0.15 mg, one has to drink 700 ml or more the beverage in order to take iron comparable to 1.0 mg iron excreted per day. On the other hand, iron content of more than 12.0 mg causes bitterness peculiar to iron, making the product unsuitable as a drink.

EXAMPLES

The examples that follow illustrates the present invention.

EXAMPLE 1

Preparation of lactoferrin

Ten liters of sulfuric esterified chitopearl(brand name), cross-linked chitosan available on the market, with sulfulic anhydride in the usual manner was filled in a column of 32 cm in diameter and 200 cm long, to which 500 liters skimmed milk was passed through at a flow rate of 200 liters per hour. After washing the column with 50 liters of 0.3M sodium chloride aqueous solution, lactoferrin adsorbed by the column was eluted with 30 liters of 1.0M sodium chloride aqueous solution. The lactoferrin solution thus obtained was desalted with small ED unit(TS-210, by Tokuyama Soda), after which it was concentrated to 10 times the original solution with UF unit (DB-2, by Amikon) and was freeze-dried.

The amnount of lactoferrin thus collected was 6 g, with measured purity of 95%. Amount of iron bound by the lactoferrin was measured to be 0.2 mg Fe/g of protein, and lactoferrin's iron-binding capacity was confirmed to be 98%.

Preparation of a bevarage containing iron

Solution containing lactoferrin and iron was prepared according to the following formulae:

| <Combination> | |
|---|---|
| lactoferrin | 600 g |
| sodium bicarbonate | 86 g |
| ferric chloride hexahydrate | 10 g |

The above ingredients were dissolved in water to make 50 liters solution. The pH and electric conductivity of the said solution are 7.5 and 1.9 mS/cm respectively. Therefore, when the said solution was heated the lactoferrin will be denatured according to the no-satisfaction of the requirements indicated in the said formulae. Therefore, after the said solution was diafiltered to eliminate low molecular ions and was adjusted to the electric conductivity of 0.12 or lower, sucrose of 10000 g, sodium citrate of 16 g, flavor of 100 g, frozen concentrated juice (Bx45, ×5 concentration) of 7000 g were added. Aqueous water was finaly added to make 100 liters. The resultant solution indicated pH of 3.7 and electric conductivity of 1.6 mS/cm and satisfied the said requirements in which the solution can be pasteurized by heat. The solution was pasteurized by using plate heat exchanger (at 93° C. for 2 to 3 seconds), bottled, held upside down for 20 seconds and cooled to obtain final iron-fortified beverage product.

The resultant beverage (iron content of 2.4 mg per 100 ml) had excellent taste and appearance.

EXAMPLE 2

Using lactoferrin prepared as in Example 1, solution containing lactoferrin and iron (solution A), and solution of beverage ingredients (solution B) were prepared according to the following formulae:

| Solution A | |
|---|---|
| lactoferrin | 600 g |
| sodium bicarbonate | 86 g |
| ferric chloride hexahydate | 10 g |

The above ingredients were dissolved in water to make 50 liters solution.

| Solution B | |
|---|---|
| sodium ferrous citrate | 48 g |
| sucrose | 9200 g |
| whole milk powder | 800 g |
| skim milk powder | 1000 g |
| parched coffee extract | 2200 g |
| table salt | 30 g |
| sodium bicarbonate | 50 g |
| sugar ester | 50 g |
| flavors | 100 g |

The ingredients were dissolved in water to make 50 liters solution.

The solution A was diafiltrated to eliminate low molecular ions and was adjusted to the electric conductivity of 0.12 mS/cm or lower. Under this condition, if the solution A and B was mixed, the mixture indicates pH 6.5 and electric conductivity of 5.5 mS/cm. Therefore, lactoferrin may be denatured by heating because of the no-satisfication of requirements of the said formulae. Therefore, it is necessary to pasteurize separately the solution A and the solution B.

The solution A was pasteurized by heat which was held at 93° C. for 2 to 3 seconds with plate heat exchanger and cooled (to 5°~10° C.), after which it was stored in the sterilized tank.

The solution B was treated with a homogenizer (homogenizing presure 160 kg/cm$^2$) and then also pasteurized by heat (held at 120° C. for 2~3 seconds) with plate heatexchanger and cooled (to 5°~10° C.), after which it was added to the above described solution A in the tank and mixed.

The mixed solution was then filled in sterillized cartons in an aseptic room to obtain iron-fortified beverage.

The beverage thus obtained (pH 5.5, iron-content 5.8 mg/100 ml) was also excellent in flavor.

EXAMPLE 3

Preparation of Iron-Lactoferrin

The sulfonated chitopearl used in the Example 1 was regenerated by passing of 1.0M sodium chloride aqueous solution and then of enough aqueous solution.

Ten liters of this regenerated chitopearl and 1,000 liters cheese whey were mixed under stirring for one hour, after which this slurry was washed with 50 liters of 0.3M sodium chloride aqueous solution. Then lactoferrin adsorbed by this slurry was eluted with 1.0M sodium chloride aqueous solution. After adding 500 mg ferric chloride, the lactoferrin solution thus obtained was passed through ion-exchange desalting resin to eliminate excess iron, and was spray-dried to obtain 48 g of iron-saturated bovine lactoferrin. The collected bovine lactoferrin had purity of 95% with iron content measuring 1.3 mg Fe/g of protein. Iron saturation was confirmed to be at least 93%.

Preparation of Iron-Fortified Beverage

Using iron lactoferrin thus obtained, iron-fortified beverage was prepared by the following formula:

| Combination: | (g) |
|---|---|
| iron-lactoferrin | 600 |
| sucrose | 11,000 |
| flavors | 100 |
| sodium ferrous citrate | 16 |
| frozen fruit juice concentrate (Bx45) | 12000 |

The above ingredients were dissolved in water to make 100 liters solution.

This iron-fortified beverage was then heated in a jacket tank to pasteurize at 70° C. for 15 minutes, followed by filling in sterilized bottles to obtained iron-fortified product.

The iron-fortified beverage thus obtained was excellent taste and appearance (pH 3.3, electric conductivity 4.36 mS, iron content of 2.5 mg/100 ml).

EXAMPLE 4

Using iron lactoferrin prepared as in Example 3, iron lactoferrin solution was made according to the following formulae.

| Combination | |
| --- | --- |
| iron lactoferrin | 600 g |
| sodium bicarbonate | 5 g |
| flavors | 100 g |
| natural colour | 10 g |

The above ingredients were dissolved in deionized water to make 100 liters solution and pasteurized. This solution thus obtained had pH 8.0 and electric conductivity of 0.1 mS/cm, then pasteurized by using plate heat exchanger at 93° C. for 3 minuts, and cooled to obtain iron-fortified beverage product.

EXAMPLE 5

This example shows the changes in lactoferrin activity during the production process of Example 2, measured by immunological method utilizing complement fixation reaction. Table 2 shows the result.

TABLE 2

| Measurement taken | Ratio of Activity |
| --- | --- |
| before mixing | 100 |
| after diafiltration | 98 |
| after pasteurization by heat | 90 |
| in finished product | 89 |

As shown in Table 2, activity of lactoferrin in finished product was 11% lower compared with lactoferrin before mixing, but the difference has no practical effect on the physiological function of lactoferrin.

EXAMPLE 6

This example shows the effect of iron-fortified beverage in the recovery from anemia.

Six-weeks-old wistar rats, made anemic (hemoglobin [Hb]concentration: 8 g/dl blood or below) by feeding with iron-eliminated feed (0.25 mg iron/100 g feed) for 3 weeks, were divided into three groups so that their average Hb concentration approximates. The first group was given the beverage obtained in the Example 2 (iron content: 5.81 mg/ml); the second group, beverage prepared as in Example 2, except that lactoferrin was eliminated and sodium ferrous citrate was used as iron preparation, these two groups were fed with iron -eliminated feed and deionized water; the third, iron -eliminated feed and deionized water only, Then, control group rats (non-anemia) were given market feed (20 mg iron/100 g) and deionized water during experiment, and each rat belonging to the group given the beverage of the present invention and to the group given the beverage containing sodium ferrous citrate as iron preparation but not lactoferrin was given 0.86 ml beverage orally each day so that iron supply would be 50 μg/rat/day.

Every two weeks since the rats began to get iron preparation, their blood was drawn to measure hemoglobin [Hb] concentration, hematocrit[Ht] value and number of red blood cells [RBC].

The results of hemoglobin [Hb] concentration, hematocrit[Ht] value and number of red blood cells [RBC] are shown in FIGS. 2, 3 and 4 respectively.

As seen in each figure, the data of the group given the iron-fortified beverage of the present invention shown in Example 1 were equivalent to the group given market feed containing iron, show its significant capability to recover from anemia. It was also clear that the group of rats given the beverage that contains sodium ferrous citrate as iron preparation but not lactoferrin show little recovery from anemia even after 70 days.

Therefore, the present invention makes it possible to obtain an iron-fortified beverage, of which iron is absorbed from the digestive tract at a high bioavailability, and which retains physiological functions of lactoferrin that coexists with iron.

We claim:

1. The method of preparing an iron-fortified beverage comprising preparing either an aqueous solution of lactoferrin, iron preparation and sodium bicarbonate, or an aqueous solution of iron lactoferrin; adjusting its electric conductivity ($\Omega$ mS/cm) and its hydrogen ion concentration (pH) so that it meets the conditions provided by the formulae:

$$\log\Omega \leq \frac{2.96}{pH} + 0.64 \quad pH < 5$$

$$\log\Omega \leq \frac{29.37}{pH} - 4.62 \quad 5 \leq pH \leq 7.9$$

$$\log\Omega \leq -0.917 \quad pH > 7.9$$

pasteurizing said solution by heat and using said solution to prepare said iron-fortified beverage.

2. The method of preparing the iron-fortified beverage according to claim 1, comprising preparing either an aqueous solution of dissolved lactoferrin, iron preparation and sodium bicarbonate and other beverage ingredients or an aqueous solution of iron lactoferrin and other beverage ingredients; adjusting its electric conductivity ($\Omega$ mS/cm) and its hydrogen ion concentration (pH) so that it meets the conditions provided by the formulae:

$$\log\Omega \leq \frac{2.96}{pH} + 0.64 \quad pH < 5$$

$$\log\Omega \leq \frac{29.37}{pH} - 4.62 \quad 5 \leq pH \leq 7.9$$

$$\log\Omega \leq -0.917 \quad pH > 7.9$$

pasteurizing said solution by heat and using said solution to prepare said iron-fortified beverage.

3. The method of preparing the iron-fortified beverage according to claim 1, comprising preparing either a first aqueous solution of lactoferrin; iron preparation and sodium bicarbonate, or a first aqueous solution of iron lactoferrin; and adjusting its electric conductivity ($\Omega$ mS/cm) and its hydrogen ion concentration (pH) so that it meets the conditions provided by the formulae:

$$\log\Omega \leq \frac{2.96}{pH} + 0.64 \quad pH < 5$$

$$\log\Omega \leq \frac{29.37}{pH} - 4.62 \quad 5 \leq pH \leq 7.9$$

$$\log\Omega \leq -0.917 \quad pH > 7.9$$

and pasteurizing said first solution by heat; separately pasteurizing a second solution of other beverage ingredients by heat; mixing said first and second solutions and using the mixed solutions to prepare said iron-fortified beverage.

4. A method of preparing iron-fortified beverage according to claim 1, wherein lactoferrin is used in an amount that makes the final concentration in the beverage 0.1-6 grams lactoferrin per 100 milliliter.

5. A method of preparing the iron-fortified beverage according to claim 1, wherein the iron preparation is used in an amount that makes the final iron concentration in the beverage 0.15-12.0 milligrams per 100 milliliter.

* * * * *

UNITED STATES PATENT AND TRADEMARK OFFICE
CERTIFICATE OF CORRECTION

PATENT NO. : 5,098,722
DATED : March 24, 1992
INVENTOR(S) : Maki Tanaka et al.

It is certified that error appears in the above-identified patent and that said Letters Patent is hereby corrected as shown below:

On the title page:
Under item [75] Inventors: change "Maki shi Tanaka" to read --Maki Tanaka--

Signed and Sealed this

Second Day of November, 1993

Attest:

BRUCE LEHMAN

Attesting Officer

Commissioner of Patents and Trademarks